United States Patent [19]
Burgess et al.

[11] Patent Number: 5,948,878
[45] Date of Patent: Sep. 7, 1999

[54] CATIONIC POLYMERS FOR NUCLEIC ACID TRANSFECTION AND BIOACTIVE AGENT DELIVERY

[76] Inventors: Stephen W. Burgess, 114 Cedar Way, Montevallo, Ala. 35115; Walter A. Shaw, 4621 Dolly Ridge Rd., Birmingham, Ala. 35243

[21] Appl. No.: 08/842,555

[22] Filed: Apr. 15, 1997

[51] Int. Cl.$^6$ .......................... C08G 63/02; C08G 63/44; C08G 69/00; C08G 63/58
[52] U.S. Cl. .......................... 528/272; 528/288; 528/299; 528/322; 528/370
[58] Field of Search .................................. 528/272, 288, 528/299, 322, 370

[56] References Cited

U.S. PATENT DOCUMENTS

| | | |
|---|---|---|
| 4,394,448 | 7/1983 | Szoka, Jr. et al. . |
| 4,833,230 | 5/1989 | Kiely et al. . |
| 5,283,185 | 2/1994 | Epand et al. . |
| 5,312,967 | 5/1994 | Kiely et al. . |
| 5,329,044 | 7/1994 | Kiely et al. . |
| 5,434,233 | 7/1995 | Kiely et al. . |
| 5,473,035 | 12/1995 | Kiely et al. . |

FOREIGN PATENT DOCUMENTS

| | | |
|---|---|---|
| WO 93/19768 | 10/1993 | WIPO . |
| WO 95/02397 | 1/1995 | WIPO . |
| WO 95/24222 | 1/1995 | WIPO . |
| WO 96/22765 | 8/1996 | WIPO . |

OTHER PUBLICATIONS

Wolfert, Margreet A., et al., "*Characterization of Vectors for Gene Therapy Formed by Self–Assembly of DNA with Synthetic Block Co–Polymers,*" Human Gene Therapy, pp. 2123–2133 (Nov. 10, 1996).

Flock, S. et al., "Dielectric constant and ionic strength effects on DNA precipitation," Biophys J. 70:3, pp. 1456–1465 (Mar. 8, 1996).

Polar Briefs, Bulletin 14, "Preparation of Cationic Liposomes & Tranfection of Cells," (Jan. 1, 1994).

Kiely et al. "Hydroxylated Nylons Based on Unprotected Esterified D–Glucaric Acid by Simple Condensation Reactions," (J. Am. Chem. Soc. 116:2, pp. 571–578 (Jul. 2, 1993).

Behr, "Gene Transfer with Synthetic Cationic Amphiphiles: Prospects for Gene Therapy," Bioconjugate Chem. 5, pp. 382–389 (1994).

Kingman, "Immune System Can't Handle Viral Vectors in the Brain," Bioworld Int'l 1:20, pp. 1,5 (May 22, 1996).

*Primary Examiner*—Nathan M. Nutter
*Attorney, Agent, or Firm*—Needle & Rosenberg, P.C.

[57] ABSTRACT

A class of polycationic polymers comprising products obtained by the copolymerization of a diprimary amine and a suitable comonomer, wherein the diprimary amine contains at least two primary amines and at least two secondary amines, and their use for nucleic acid transfection, and the delivery of suitable anionically charged bioactive molecules.

16 Claims, No Drawings

CATIONIC POLYMERS FOR NUCLEIC ACID TRANSFECTION AND BIOACTIVE AGENT DELIVERY

BACKGROUND OF THE INVENTION

1. Field of the Invention

The invention is in the field of synthetic polycationic polymers, and the use of synthetic polycationic polymers as nucleic acid transfection agents and anionically charged bioactive agent delivery vehicles. In a particular embodiment the invention relates to polycationic polymers obtained from the copolymerization of multifunctional diprimary amines and dicarboxylic monosaccharides.

2. Background Art

In recent years gene therapy, i.e., the use of genetic materials for medical treatments, has received tremendous attention in scientific and academic circles as the pharmaceutical, commercial, and clinical potential of gene therapy has gradually emerged. The introduction of genes into cells of various origins, often referred to as gene transfection, is a critical component of any therapeutic or clinical regime.

Several different approaches have been developed for gene transfer. These include the use of viral based vectors (e.g., retroviruses, adenoviruses, and adeno-associated viruses) (Drumm, M. L. et al., *Cell* 62:1227–1233 (1990); Rosenfeld, M. A. et al., *Cell* 68:143–155 (1992); and Muzyczka, N., *Curr. Top. Micro. Immuno.* 158:97–129 (1992)), charge associating the DNA with an asialorosomucoid/poly L-lysine complex (Wilson, J. M. et al. (1992)), charge associating the DNA with cationic liposomes (Brigham, K. L. et al. (1993)) and the use of cationic liposomes in association with a poly-L-lysine antibody complex (Trubetskoy, V. S. et al., *Biochem. Biophys. Acta* 1131:311–313 (1993)).

To date, viral vectors have exhibited the highest levels of transfection efficiency for nucleic acids. Viral vectors have been particularly effective in in vivo systems, in contrast to non-viral vectors whose in vivo transfection efficiency has lagged. (Hanaria, E. G. et al., *Am. Jnl. Microencapsulated.* 99(5):537–52 (1995)) Although viral vectors are typically very effective at transfecting the cell, the use of viral vectors suffers from a major disadvantage. In particular, because the method infects an individual cell with a viral carrier, a potentially life threatening immune response to the treatment can develop. (Kingman, *BioWorld Int.,* 1(20):1 (1996))

Although non-viral based transfection systems have not exhibited the efficiency of viral vectors, they have received significant attention, in both in vitro and in vivo research, because of their theoretical safety when compared to viral vectors. Synthetic cationic molecules, have been reported which reportedly "coat" the nucleic acid through the interaction of the cationic sites on the transfection agent and the anionic sites on the nucleic acid. The positively charged coating reportedly interacts with the negatively charged cell membrane to facilitate the passage of the nucleic acid through the cell membrane by non-specific endocytosis. (Schofield, *Brit. Microencapsulated. Bull.,* 51(1):56–71 (1995)) These compounds have, however, exhibited considerable sensitivity to natural serum inhibition, which has probably limited their efficiency in vivo as gene transfection agents. (Behr, *Bioconjugate Chem.,* 5, 382–389 (1994))

A number of attempts have been made to improve the efficiency of lipid-like cationic transfection agents, some involving the use of polycationic molecules. For example, several transfection agents have been developed that contain the polycationic compound spermine covalently attached to a lipid carrier. Behr, *Bioconjugate Chem.,* 5, 382–389 (1994), discloses a lipopolyamine and shows it to be more efficient at transfecting cells than single charge molecules (albeit still less efficient than viral vectors). The agent reported by Behr was, however, toxic, and caused cell death.

Past attempts at nucleic acid transfection have also experienced difficulties with DNA precipitating out of solution. The problem is especially acute in in vivo applications wherein higher concentrations of DNA are often employed that create solubility problems for the DNA/carrier compound systems. Solutions to DNA precipitation have been addressed by research such as described in J. Bio. Chem. 271, no. 10 March 8, pp. 5656–5661. There, it was found that precipitation of DNA could be avoided by significantly stepping up the concentration of mono and multi-valent cations. While partly successful solubilizing the DNA/carrier complex, increasing ionic strength had toxic effects upon the transfected cells. Thus, there is a need in the art to enhance DNA uptake, in the presence of serum, which includes high DNA concentration levels in the nucleic acid/carrier system that are not prone to loss of solubility of DNA and without causing toxicity to the cells.

The present invention provides a new class of non-viral polymeric vectors that can be used for both in vitro and in vivo transfer of biologically active molecules. In particular, these vectors can be used for gene transfer applications. These polycationic non-lipid compounds can achieve gene transfer efficiencies in vitro that are superior to commercially available cationic liposome preparations. Further, their low toxicity and lack of serum inhibition is consistent with in vivo use. The present invention provides a vector that can achieve in vivo gene transfer efficiencies that compare favorably to viral vector systems. The present invention further provides a method to increase the capacity of solutions to carry complexes of nucleic acids and the polymeric vector without precipitation or toxic ionic effects on cells.

Furthermore, the unique polycationic structure of this class of polymers associates with many suitable bioactive molecules, including proteins and other compounds that possess multiple anionic sites. The polymer can act as a carrier to deliver the associated bioactive molecule, in vivo or in vitro, to the cells of interest for the bioactive molecule.

SUMMARY OF THE INVENTION

In one aspect the invention provides a complex comprising a nucleic acid and a transfection agent, wherein a) the transfection agent is obtained by the copolymerization of a diprimary amine and a suitable comonomer; and b) the diprimary amine contains at least two primary amines and at least two secondary amines.

In another aspect the invention provides a polymer obtained by the copolymerization of a diprimary amine and a suitable comonomer, wherein the diprimary amine contains at least two primary amines and at least two secondary amines.

In still another aspect of the invention there is provided a polymer, and a complex between the polymer and a nucleic acid, wherein:

a) the polymer comprises a backbone that comprises repeating units: (V) and (X), wherein (X) is selected from (VI) and (VII), and wherein (V), (VI), and (VII) have the formulae:

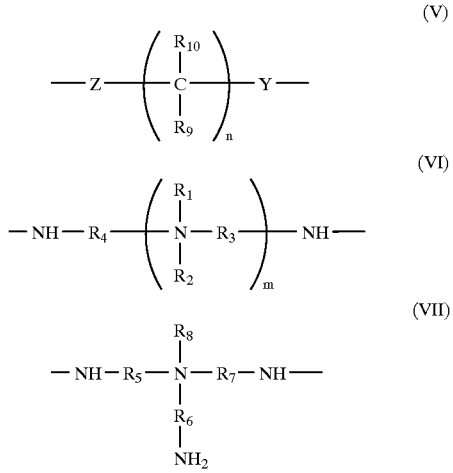

b) Z and Y are each, independently, selected from the group consisting of a valence bond, carbonyl and amine moieties;

c) each of the $R_1$, $R_2$, and $R_8$ functionalities is, independently, selected from the group consisting of hydrogen, aromatic hydrocarbons, and aliphatic hydrocarbons;

d) each of the $R_3$, $R_4$, $R_5$, $R_6$, and $R_7$ functionalities is, independently, an aliphatic hydrocarbon or a valence bond;

e) each of the $R_9$ and $R_{10}$ functionalities, is, independently, selected from the group consisting of a hydrogen, hydroxyl, aromatic hydrocarbon, aliphatic hydrocarbon, amide, aryl halide, azo, carbamate, carboxylic ester, ether, thioether, fluorescent derivative, and sulfonic acid moieties, and polymeric repeating units; units;

f) n is an integer equal to or greater than one; and g) m is an integer equal to or greater than two.

In yet another aspect of the invention there is provided a complex formed by the charge association between the polymer and a suitable anionically charged bioactive molecule such as a protein, polypeptide, or peptide.

In still another aspect of the invention there is provided a method of forming a complex of a nucleic acid and a transfection agent comprising mixing a diluted volume of nucleic acid with a corresponding diluted volume of transfection agent to obtain a diluted complex solution, wherein the transfection agent and nucleic acid are present in said diluted complex solution at a weight ratio of about 1:10, and dehydrating the diluted complex solution.

There is further provided by the invention a complex of nucleic acid, polyethylene glycol, and a transfection agent, formed by:

a) mixing a transfection agent with polyethylene glycol to obtain a mixture A, b) mixing a nucleic acid with polyethylene glycol to obtain a mixture B, and c) mixing mixture A with mixture B.

The present invention may be further understood by reference to the following detailed description.

DETAILED DESCRIPTION OF THE INVENTION

As used herein and in the claims, "transfection agent" means any chemical agent capable of facilitating the entry of a nucleic acid into a eukaryotic cell.

As used herein and in the claims, "nucleic acid" means a polymer of nucleotides, and specifically includes plasmids, coding DNA sequences, mRNAs, and antisense RNA molecules. A nucleic acid can be single- or double-stranded. The nucleic acids can also contain one or more substitute linkages. These substitute linkages include conventional alternative linkages such as phosphorothioate and phosphoramidate, and are synthesized as described in generally available literature. Nucleic acids also include those nucleotides in which the sugar moiety has been modified by, for example, substitution of one or more hydroxyl groups with halogen, aliphatic groups, or functionalized as ethers, amines, or wherein the ribose or deoxyribose is replaced with other functionally equivalent structures. In particular, the sugar-phosphate backbone may be replaced with a non-carbohydrate backbone such as a peptide or other type of polymer.

As used herein and in the claims, the term diprimary amine means any amine that possesses two or more primary amine functionalities.

As used herein and in the claims, the term secondary amine includes amine moieties having at least two pendent hydrocarbon groupings, and also includes, in the appropriate context, tertiary and quaternary amines.

As used herein and in the claims, the terms "dihalide," "dialcohol," and "dicarboxylic acid," mean any compound that possesses two or more halide, alcohol, or carboxylic acid functionalities respectively.

As used herein and in the claims, "a" can mean one or more, depending upon the context in which it is used.

As used herein and in the clams, aliphatic and aromatic hydrocarbons include both substituted and unsubstituted compounds, wherein the substitution can occur in the backbone or pendent groupings of the hydrocarbon. Aliphatic compounds may be branched or straight chained.

This invention relates to a novel class of polycationic polymers having effective nucleic acid transfection properties and bioactive agent delivery attributes. The polymers are obtained from the copolymerization of a diprimary polyamine monomer with a suitable comonomer, typically a dicarboxylic acid, dihalide, or dialcohol. Both of the comonomers can be selected to enhance the degree and efficiency of transfection. For example, comonomers can be selected based upon the density and distribution of the cationic sites on the comonomers to obtain transfection agents that are tailored to the anionic charge distribution of the nucleic acid being transfected, and the anionic charge distribution of the type cell being targeted. Various substituents can also be incorporated into the polymer or complexed with the polymer, also to affect the properties of the polymer, and to improve the ultimate transfection efficiency of the polymer.

The present invention provides (1) a class of polycationic polymers, (2) a class of complexes comprising these polymers with nucleic acids, and (3) a class of complexes comprising these polymers with suitable anionically charged bioactive agents. The class of polycationic polymers comprises products obtained by the copolymerization of a diprimary amine and a suitable comonomer, wherein the diprimary amine contains at least two primary amines and at least two secondary amines.

By "at least two" primary amines and "at least two secondary amines" is meant that the diprimary amine has minimally two of each amine, but can preferably also have three, four, five, six, or seven of each amine. In a particularly preferred embodiment, the diprimary amine has two primary amines and four secondary amines.

The suitable comonomer is selected generally from any compound known to copolymerize with the diprimary amine under suitable copolymerizing conditions. Examples of suitable comonomers include, for example, dicarboxylic acids, dicarboxylic acid esters, dicarboxylic chlorides, dicarboxylic anhydrides, dicarboxylic imidazolides, dihalides, and dialcohols.

The copolymerization of the comonomers may be performed generally by methods known in the art, including by condensation reactions. Examples of suitable copolymerization techniques are described in detail in Kieley et al., *J. American Chemical Society*, 116, 571–578 (1994), Kieley et al., U.S. Pat. Nos. 5,434,233, 5,312,967, 5,473,035, 5,833,230, and 5,329,044, and Dewar et al., U.S. Pat. No. 3,225,012.

In a particular embodiment the invention provides a class of polymers comprising polyamides obtained by the copolymerization of diprimary amines and dicarboxylic monosaccharides. Preferred polyamides can be represented by the following general formula:

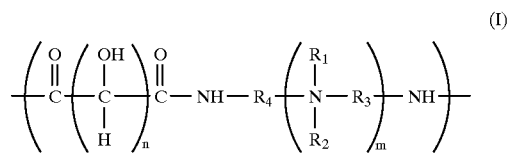

(I)

$R_1$ and $R_2$ may be hydrogen, or any aromatic or aliphatic hydrocarbon that imparts to the secondary amine (i.e. the amine group located within the parentheses in formula (I)) a cationic charge. If $R_1$ and $R_2$ are hydrocarbons, therefore, they may contain substituent groups that lend desirable properties to the compound, provided the substituent groups do not interfere with the cationic charge of the secondary amine. Thus, while alkyl groups having less than about three carbon atoms are preferred, and methyl groups are even more preferred, hydrogen is perhaps the most desirable constituent for the $R_1$ and $R_2$ moieties, because hydrogen atoms generally contribute the most concentrated cationic charge to the secondary amine. The $R_1$ and $R_2$ moieties can vary among the m number of moieties within a particular comonomer, and also among comonomers within the polymer.

$R_3$ and $R_4$ are generally selected from the group of aliphatic hydrocarbons having at least one carbon atom. The size of the $R_3$ and $R_4$ moieties can vary among the amines used to prepare a copolymer, and may be chosen based upon the density or distribution of cationic moieties in the copolymer one is attempting to prepare. They may contain substituent groups that lend desirable properties to the compound. $R_3$ and $R_4$ may preferably comprise an alkyl moiety having from 1 to 5 carbon atoms, and more preferably comprise ethylene.

While $R_3$ and $R_4$ typically are aliphatic compounds, they may also be omitted, in which case $R_3$ and $R_4$ would represent valence bonds. Moreover, $R_3$ may vary within the m repeating units, or among polymeric repeating units. $R_4$ may similarly vary among polymeric repeating units where, for example, more than one comonomer is employed in the copolymerization reaction.

The number m of secondary amine moieties can vary among copolymers and among amine monomers within a copolymer. The number m of secondary amine moieties determines the number of cationic sites that will be present in each repeating unit of the copolymer, and should be chosen based upon the number and density of cationic charges one wishes to obtain from the polymer eventually formulated. While the number m should be at least two, in a more suitable embodiment m is greater than two. For example, it can be two, three, four, five, six or seven. A particularly suitable number m is four.

The number n of alcohol moieties can also vary among copolymers and among comonomers within a copolymer. The number n of alcohol moieties determines the degree to which the cationic comonomers will be separated within the polymer, and should be chosen based upon the density of cationic charges one wishes to obtain from the polymer eventually formulated. The number n of alcohol moieties should be at least one and should generally not exceed about 20. The number n more suitably ranges from about 2 to about 6, and most suitably is 4. If there is more than one alcohol moiety, the invention encompasses all isomers of the particular compound that contains the more than one alcohol moiety.

The polyamide represented by formula (I) has a charge profile that suggests its spontaneous complexation with a nucleic acid or suitable bioactive agent having anionic charge association sites. In particular, the polyamide can form a complex with a nucleic acid or bioactive agent when the cationic moieties on the polyamide ionically associate with the polyanionic charges of the phosphate groups located on the nucleic acids or anionic groups on the bioactive agent. Particularly suitable polyamides, therefore, possess cationic charge profiles that correspond favorably to the anionic charge profile of a nucleic acid to be complexed with the polyamide. This complexation has been demonstrated particularly for poly (3', 6', 9', 12'-aza-tetradecylmethylene D-glucaramide). The molecular weight of a polyamide may also affect its suitability for a particular transfection application. Thus, although the polyamide preferably ranges in size generally from one monomeric unit to about 100,000 AMU, a particularly suitable molecular weight for the polyamide is between about 12,000 and about 20,000 AMU.

The ionic association of the polymer/nucleic acid charges neutralizes the anionic charges on the nucleic acid and allows the complex to interact and bind more favorably with the negatively charged cell surface. If an excess of cationic sites is present on the polymer, i.e. more than is necessary to neutralize the anionic charges on the nucleic acids, these excess cationic charges may facilitate the attraction of the complex to the ionically charged surface of the cell, thereby facilitating entry of the complex into the cell. The polyamides may also compact the nucleic acids upon complexation, which further enhances the likelihood of entry.

Preferred diprimary amines for carrying out the copolymerization include compounds of the general formula:

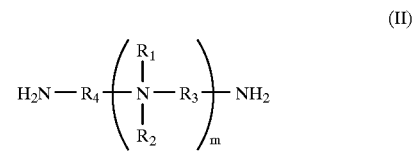

(II)

wherein $R_1$, $R_2$, $R_3$, $R_4$, and m are defined as above with respect to formula (I). Suitable diprimary amines include spermine and decamethylene tetramine. A particularly suitable diprimary tetrasecondary amine is pentaethylene hexamine.

As seen from the foregoing structure, suitable amines for practicing the invention have at least two end amino groups, also referred to as "primary" amines. Suitable amines can have more than two primary amino groups, however, and could include, for example, diprimary amines of the following general structure:

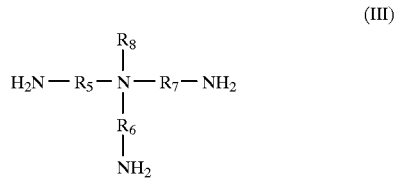

(III)

wherein $R_5$, $R_6$, and $R_7$ may be chosen from the groups that comprise the $R_3$ and $R_4$ moieties in the polymer of formula (I) discussed above, and $R_8$ may be chosen from the groups that comprise the $R_1$ and $R_2$ moieties in the polymer of formula (I) discussed above.

preferred comonomers for the diprimary amines include dicarboxylic acids such as dicarboxylic monosaccharides. Dicarboxylic monosaccharides can be represented generally by the formula:

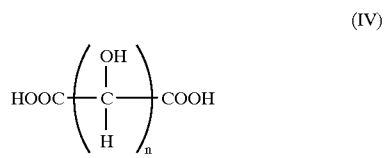

(IV)

wherein n is defined as in formula (I). Examples of suitable dicarboxylic monosaccharides include glucaric acid, galactaric acid, xylaric acid, and their various isomers.

Because dicarboxylic monosaccharides are derivatives of monosaccharides they can be readily obtained from the synthesis of plants and other natural sources. The dicarboxylic derivatives of the monosaccharides are particularly suitable for obtaining the polyamides of this invention because they can be reacted with a diprimary amine to obtain a polycationic polyamide by condensation processes known in the art. Derivatives of dicarboxylic acids, such as dicarboxylic esters, acid chlorides, anhydrides, and imidazolides of dicarboxylic acids, can also be reacted with the diprimary amines, under appropriate reaction conditions, also to obtain suitable polyamides.

The use of dicarboxylic monosaccharides as comonomers is especially suitable for transfection and biological applications because the monosaccharides are water soluble and miscible in aqueous vehicles. These properties typically are transferred to the polyamide upon copolymerization and thereby also contribute solubility and miscibility to any polyamide into which the monosaccharides are incorporated. Because the resultant polyamide is water soluble and miscible in water, it can be readily transported to cells in vivo by known biological processes, and acts as an effective vehicle for transporting agents complexed with it. Moreover, because monosaccharides are staples in the diets of many living organisms, most are nontoxic and biodegradeable.

Other aliphatic dicarboxylic comonomers (and derivatives of such comonomers) can be selected for the comonomer in which the length of the aliphatic chain (excluding the carboxyl moieties) is between zero and about twenty, and the degree to which the comonomer is hydroxylated is from zero to 100%. The degree of hydroxylation can be varied, for example, depending upon the degree of water solubility one desires from the comonomer (and resultant copolymer). The length of the aliphatic chain can similarly be shortened or lengthened in order to increase or decrease the density of cationic sites on the resultant copolymer.

Because the invention is not limited to monosaccharides, but only to comonomers that copolymerize with the diprimary amines of this invention, various substituents can be incorporated into the comonomer. For example, the hydroxyl and hydrogen groups on the aliphatic chain of the monosaccharides can be substituted with aromatic and aliphatic hydrocarbons, amides, aryl halides, azo, carbamate, caroxylic esters, ethers, thioethers, fluorescent derivatives, and sulfonic acids. One is often able to increase the hydrophobicity of the polymer (where hydrophobicity is desired) by alkylating the secondary amines with lone chain hydrocarbons.

Comonomers other than dicarboxylic acids (and their derivatives) can also be used to obtain suitable polycationic polyamides. For example, dialcohols and dihalides, which are also known to copolymerize with diprimary amines, can be used as comonomers in the present invention. Dicarboxylic acid, dialcohol, and dihalide comonomers can further contain secondary amino groups that can contribute additional cationic charges to the resultant polymer. As with the monosaccharides, these comonomers can also be substituted with varying substituents to obtain polymers with desired properties. Examples of suitable alternative compounds include, for example, compounds of the following formulae:

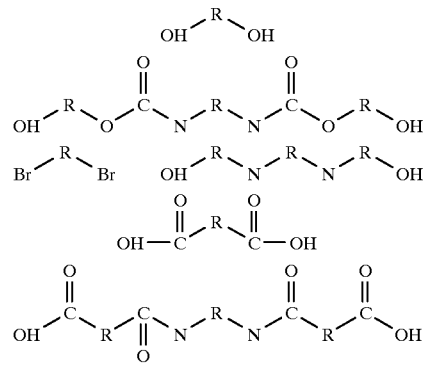

wherein R can be any aliphatic or aromatic hydrocarbon, optionally substituted in its backbone or pendent groupings with any suitable grouping including amides, aryl halides, azo, carbamate, carboxylic esters, ethers, thioethers, fluorescent derivatives, and sulfonic acids. Moreover, R can vary within any of the particular compounds.

For convenience, compounds of the foregoing general formulae will generally be referred to herein and in the claims as "dicarboxylic acids," "dihalides," and "dialcohols," because each of the compounds has at least two functional groups. The invention is not limited to compounds having only two functional groups, however, and includes copolymers wherein the comonomer possesses three or more functional groups, because these comonomers will also copolymerize with diprimary amines. As noted previously, the terms dihalides, dicarboxylic acids, and dialcohols, are also used to refer to compounds having two or more functional groups.

The structure of the polymer can also be altered, by known techniques, to optimize the transfection and delivery efficiency of the polymer for each cellular target on the basis of the physiological and biological characteristics of that target. For example, the efficiency of gene delivery to cells can be enhanced by the addition of peptides with the nuclear-targeting signal of simian virus 40 to the polymer. Several protein ligands are also known that can be covalently coupled to the polymer and then incorporated into a ligand-nucleic acid complex. The resulting complexes retain their ability to interact specifically with cognate receptors on the target cell.

Another method to improve the efficiency of gene delivery is to enhance the release of DNA from the endosome after it has entered the cell. Adenoviral particles can be coupled to the polymer to increase this efficiency. Synthetic peptides can also be designed and incorporated into the polymer in order to enhance endosomal release.

The invention also provides a polymer, and a complex comprising the polymer and nucleic acid, wherein:

a) the polymer comprises a backbone that comprises repeating units (V) and (VI) or (VII) of the formulae:

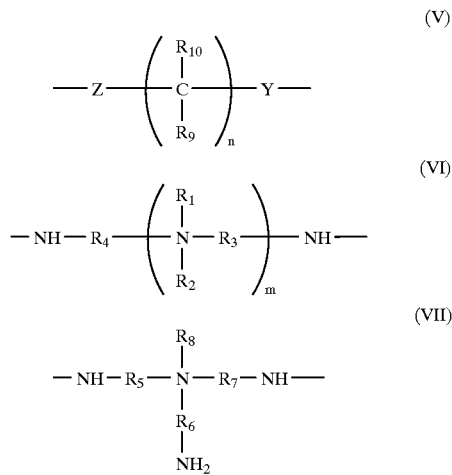

b) Z and Y are each, independently, selected from the group consisting of a valence bond, carbonyl and amino units;

c) the $R_1$–$R_8$ functionalities are as defined in formulas I, II, and III herein;

d) each of the $R_9$ functionalities, and each of the $R_{10}$ functionalities, is, independently, selected from the group consisting of a hydrogen, hydroxyl, aromatic hydrocarbon, aliphatic hydrocarbon, amide, aryl halide, azo, carbamate, carboxylic ester, ether, thioether, fluorescent derivative, and sulfonic acid moieties, and polymeric repeating units; and e) n is an integer equal to or greater than one and m is an integer equal to or greater than two.

Particularly suitable carbonyl and amino units include —CO—, —$NR_1R_2$—CO—O—$CR_1R_2$—, —$NR_1R_2$—$CR_1R_2$—, and —$NR_1R_2$—CO—$CR_1R_2$—CO—.

The complexes of this invention are of general use for gene transfer and bioactive agent delivery with respect both to cell type and size of nucleic acid or bioactive agent because the transfection is driven by non-specific ionic interactions. Any selected cell into which transfection of a nucleic acid or delivery of a bioactive agent (via transfection or otherwise) would be useful can be targeted by this method, by administering the complex in a suitable manner to bring the complex into contact with the selected cell, as is known in the art. Cells can be within a tissue or organ, for example, supplied by a blood vessel into which the complex is administered. Alternatively, for example, the complex can be directly injected into the target tissue or organ. As a further example, the lungs can be targeted by inhalation or intratracheal injection. The invention has application to all eukaryotic cells; it can be used particularly for mammalian cells and subjects, such as humans, cows, horses, sheep, pigs, rats, and mice. Some examples of cells that can be targeted by this inventive method include fibroblasts, epithelial cells, endothelial cells, blood cells and tumor cells, among many.

Because the monosaccharide backbone in one embodiment is both biodegradable and regularly imported into living cells as part of normal biosynthetic processes, it is non-toxic, which offers a distinct advantage over viral vectors when used as transfection agents. Similarly because monosaccharides are a necessary component of any living organism and do not generally contain natural binding sites for serum, the monosaccharide backbone is not negatively impacted by circulating serum proteins such as heparin and albumin. Complexes formed with the polymers thus reach targeted cells intact without significant serum inhibition, in contract to polycationic lipids which are substantially impacted by natural systemic serums.

The amounts of polymer and nucleic acid or suitable bioactive agent in the complex may be chosen to obtain a complex, when mixed with the nucleic acid or bioactive agent, that has a net cationic charge. That is, the polymer may contribute more cationic charges than the anionic charges contributed by the nucleic acid or bioactive agent. A particularly suitable polymer to DNA ratio, using the poly (3' 6', 9', 12'-aza-tetradecylmethylene D-glucaramide) polymer and a reporter plasmid such as PcLuc4, evaluated by transfection of the human sarcoma cell line HT1080, ranges from about 15–20 parts polymer to about 2–3 parts DNA. A particularly suitable ratio is about 10:1 (wt./wt.). A similar optimum would be expected when transfecting other cell lines. If other nucleic acids or transfection agents are employed, then a suitable ratio of transfection agent to nucleic acid can be readily determined by routine experimental protocol and/or by extrapolation from the above example. For any selected copolymer, the ratio of copolymer to nucleic acid can be optimized in vitro prior to in vivo use.

The amount of DNA that is carried in solution can also influence the degree of transfection by the complex. As previously noted, however, the concentration of DNA in solution is often limited by its tendency to precipitate at higher concentrations. In some applications, the DNA concentration in solution is limited to about 1.5 g/l. Increased amounts of DNA may be carried with the polymer in solution, however, without precipitation of the DNA, if one of two protocols is followed. In the first protocol, the polymer and nucleic acid are mixed separately in substantially equivalent volumes of diluent. The complexes are then formed by combining the mixtures. The volume of the combined mixture can then be reduced by evaporation or lyophilization. By following this protocol it is often possible to obtain solutions carrying 25 grams of DNA per liter of solution, at a wt. ratio of polymer to DNA of about 10:1.

In the second protocol for increasing the concentration of DNA in solution without precipitation, nucleic acid and polymer are mixed separately with a suitable carrier enhancer such as polyethylene glycol (6000), and then mixed together. The final mixture is ready to use. Like the first protocol, mixture of each component must occur outside the presence of the other or else both will precipitate out of solution as their respective amounts are added.

Suitable delivery and transfection conditions include cell and complex temperature between about 18° C. and about 42° C., with a preferred temperature being between about 22° C. and about 37° C. For administration to a cell in a subject, the complex, once in the subject, will of course adjust to the subject's body temperature. For ex vivo administration, the complex can be administered by any standard method that would maintain viability of the cells, such as by adding the complex to a culture medium (appropriate for the target cells) and adding this medium directly to the cells. The medium used in this method should be aqueous and non-toxic so as not to render the cells non-viable. In addition, the medium can contain nutrients for maintaining viability of cells, if desired.

The complex can be administered in vivo by parenteral administration, e.g., by intravenous injection including regional perfusion through a blood vessel supplying the tissue(s) or organ(s) having the target cell(s). Injectables can be prepared in conventional forms, such as liquid solutions, suspensions, or emulsions. A slow release or sustained release system can also be used, allowing the maintenance of a constant level of dosage.

Other means of administration can include inhalation of an aerosol, subcutaneous, intraperitoneal, or intramuscular injection, topical administration such as to skin wounds and lesions, direct transfection into, e.g., bone marrow cells prepared for transplantation and subsequent transplantation into the subject, and direct transfection into an organ that is subsequently transplanted into the subject. Further administration methods can include oral administration, particularly when the complex is encapsulated, or rectal administration, particularly when the complex is in suppository form.

A composition can include the present complex and a pharmaceutically acceptable carrier suitable for the selected mode of administration. A pharmaceutically acceptable carrier includes any material that is not biologically or otherwise undesirable, i.e., the material may be administered to an individual along with the selected complex without causing any undesirable biological effects or interacting in a deleterious manner with any of the other components of the pharmaceutical composition in which it is contained. A composition can further include other medicinal agents, pharmaceutical agents, adjuvants, diluents, etc., as long as they do not interfere with the action of the complex. Actual methods of preparing such dosage forms are known or will be apparent to those skilled in the art. (See, e.g., Martin, E. W. *Remington's Pharmaceutical Sciences*, latest edition, Mack Publishing Co., Easton, Pa.)

Optimal time lengths and conditions for any specific complex and any specific target cell can readily be determined, given the teachings herein and knowledge in the art. Specifically, if a particular cell type in vivo is to be targeted, for example, by regional perfusion of an organ or tumor, cells from the target tissue can be biopsied and optimal dosages for import of the complex into that tissue can be determined in vitro, as described herein and as known in the art, to optimize the in vivo dosage, including concentration and time length. Alternatively, culture cells of the same cell type can also be used to optimize the dosage for the target cells in vivo. In general, a dosage will be similar to dosages typically used to administer polycationic liposomes.

For either ex vivo or in vivo use, the complex can be administered at any effective concentration. Culture experiments have shown that poly (3', 6', 9', 12'-aza-tetradecylmethylene D-glucaramide) has little effect on human carcoma cell line HT1080 viability at concentrations as high as 60 ug/mL.

Depending on the intended mode of administration, the pharmaceutical compositions may be in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. The compositions can include, as noted above, an effective amount of the selected drug in combination with a pharmaceutically acceptable carrier and, in addition, may include other medicinal agents, pharmaceutical agents, carriers, adjuvants, diluents, etc.

For many of the reasons that the polymer is an effective nucleic acid transfection agent, it is also an effective carrier or delivery vehicle for natural and synthetic bioactive agents that contain anionic charges, and that preferably have multiple or poly-anionic sites. Among other advantages, the polymer can be tailored to the charge profile of the particular bioactive molecule to be delivered, it can compact long chained bioactive molecules in order to facilitate their delivery, excess cationic sites on the polymer can selectively charge associate with negative charges on the surfaces of cells to facilitate transfection, and the monosaccharide backbone is nontoxic and compatible with normal biosynthetic processes. As it does with DNA, the polymer can charge associate with suitable natural and synthetic polymers having single or multiple anionic sites. Once this complex is formed, the suitable bioactive agent can be delivered, in vitro or in vivo, to a particular cell or location within a subject.

The polymer is especially suited for delivering multianionic and polyanionic proteins in vivo. The anionic charges on suitable proteins can be contributed typically via conjugation or by the pendent functional groups on the amino acid sequence. Thus, suitable conjugated proteins typically have multiple anionically charged prosthetic groups, and can include, for example, many lipoproteins and phosphoproteins. Proteins comprising aspartic and glutamic acids, containing anionically charged carboxylic groups, are also suitable proteins for delivery by the polymeric carriers of this invention. Hydroxy amino acids that have been phosphorylated by, for example, adenosine triphosphate ("ATP"), to yield phosphoserine, phosphothreonine, or phosphotyrosine, may also contribute to the anionic charges of suitable proteins, as may hydroxy amino acids that are sulfated by, for example, 3'-phosphoadenosine-5'-phosphosulfate to obtain sulfated proteins and other polyamino acids. Extra carboxyl groups may also be added, for example, to the aspartic acid and glutamic acid residues of some proteins such as, for example, in prothrombin, to obtain anionically charged proteins.

The foregoing proteins, polypeptides, and peptides are, of course, merely illustrative of the general class of polyamino acids and other bioactive agents that may be complexed and delivered by the polymers of the instant invention. Other anionically charged bioactive agents, such as sulfated glycolipids (including sulfated gangliosides), and heparin sulfate, may also be obtained or synthesized and subsequently complexed and delivered with the polymers of the instant invention. Moreover, while the polymer is particularly suited for delivering bioactive agents that have multiple or poly-anionic sites, it can also be used to deliver bioactive agents having as few as one anionic site. Lyso phosphatidic acid is another example of the suitable anionically charged bioactive agents that can be delivered in the complexes of the present invention.

The percentage of anionically charged amino acids or other structural unit on the protein, peptide, polypeptide, or other suitable bioactive agent is not critical to the invention, and generally any bioactive agent having anionic sites, and preferably having a net anionic charge, is suitable for delivery through the complexes of the present invention. Moreover, the polymer can generally charge associate with suitable proteins and other large bioactive agents regardless of size or molecular weight.

Complexes may be formed between suitable bioactive agents and the polymer in a manner comparable to the manner in which DNA/polymer complexes are formed. In particular, the complexes can be formed simply by mixing the polymer and bioactive agent in a suitable aqueous buffer. It may be desirable, however, when preparing complexes between the polymer and high molecular weight proteins and other bioactive agents, to compensate for the precipitation that typically occurs during efforts to solubilize such complexes. Such precipitation can be avoided by, for example, employing the methods discussed herein for limiting precipitation from complexes of DNA and the polymer. Other methods include those set forth in Flock et al., *Biophys. J.*, 70:3, 1456–65 (1996); Pelta et al., *J. Biol. Chem.*, 271:10, 5656–82 (1996); and Sikarov et al., *Biophsy. J.*, 67, 1387–92 (1994), which are hereby incorporated in their entirety by this reference.

Statement Regarding Utility

The present method, which provides an effective method for importing nucleic acids into cells and delivering bioactive agents to cells, has many uses, both in vivo and ex vivo. The in vivo effectiveness can be at least partly attributed to the minimal serum inhibition experienced by the polymers in vivo, in addition to the biocompatibility and minimal toxicity associated with the class of polymers. In vivo, the method can be used to deliver into cells DNA for gene therapy (e.g., to provide the CFTR gene in cystic fibrosis patients); and RNA for antisense therapy (e.g., to inhibit growth as in inhibiting expression in cancer cells). Human airway epithelium with CFTR gene anomalies is particularly sensitive to gene transfer of PcLuc4 plasmid DNA using 3', 6', 9', 12'-aza-tetradecylmethylene D-glucaramide. Ex vivo, the method allows efficient transfection of cells without performing cell-damaging procedures. Therefore, this method is useful ex vivo in any method that utilizes transfection, such as transfecting of reporter genes into cells to screen for compounds that affect expression of the reporter gene, and for transfecting bone marrow cells, blood cells, cells of an organ for subsequent transplantation into a subject, or culture cells, with a gene to effect protein expression in the cells.

The present invention is more particularly described in the following examples which are intended as illustrative only since numerous modifications and variations therein will be apparent to those skilled in the art.

EXAMPLES

Example 1

Poly (3' 6', 9', 12'-aza-tetradecylmethylene D-glucaramide) can be prepared as follows:

To a methanol solution of ethyl ester glucaric acid (18 mmoles) is added a methanol solution of pentaethylenehexamine (21.6 mmoles). The clear solution is stirred overnight at room temperature. The solution is then diluted 2-fold with methanol and precipitated with stirring by adding at least a 5-fold excess of ethanol. The glutinous precipitate that forms is isolated by decanting the supernatant and dissolving in ethanol/deionized water (1:1, v/v). The resulting clear solution can be used directly or diluted with water for complexing genetic material. The theoretical yield of the reaction described above is approximately 8 g. The actual yield for this reaction is typically about 4.5 g. Presumably the weight is lost in low molecular weight polymers and unreacted material which are soluble in the ethanol solution used to precipitate the large polymers. Molecular weight determinations of the polymer using mass spectrometry indicate the polymer is approximately 12,000–20,000 amu.

Example II

Poly (3', 6', 9', 12'-aza-tetradecylmethylene D-glucaramide), the copolymerization product of ethyl ester glucaric acid and pentaethylene hexamine, was used to transfect a PcLuc4 plasmid into HT-1080 human carcoma cells. Poly (3', 6', 9', 12'-aza-tetradecylmethylene D-glucaramide) and PcLuc4 plasmid were used at a ratio of plasmid to polymer of 2–3 micrograms to 15–20 micrograms in a final volume of 1 ml of physiological saline solution. Efficient transfection was achieved.

Example III

A solution containing a complex of poly (3', 6', 9', 12'-aza-tetradecylmethylene D-glucaramide) and DNA can be prepared as follows:

4.8 ml of $H_2O$ are mixed with 200 microliters of a physiologic salt solution to yield a final volume of 5 ml. The solution is split into two equal portions. To one portion (2.5 ml) 500 micrograms of polymer is mixed. To the other portion 50 micrograms of plasmid DNA is mixed. After mixing, the solutions are mixed together and then dehydrated by evaporation or lyophilization to a final volume of 200 microliters.

Example IV

A solution containing a complex of poly (3', 6', 9', 12'-aza-tetradecylmethylene D-glucaramide) and DNA can also be prepared as follows:

100 microliters of a 30% PEG (6000) are aliquoted into each of 2 tubes. To one tube is added 50 micrograms of plasmid DNA. To the other tube is added 500 micrograms of polymer. Each tube is vortexed and then the volume of the tubes are mixed and vortexed. The resulting solution is ready for use in transfecting cells.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

What is claimed is:

1. A product selected from the group consisting of polymers (i) obtained by the copolymerization of a diprimary amine and a suitable comonomer, wherein the diprimary amine is a precursor to repeat unit (VI) or (VII), and polymers (ii) comprising a backbone that comprises repeating units (V) and (X), wherein (X) is selected from (VI) and (VII), and wherein (V), (VI), and (VII) have the formulae:

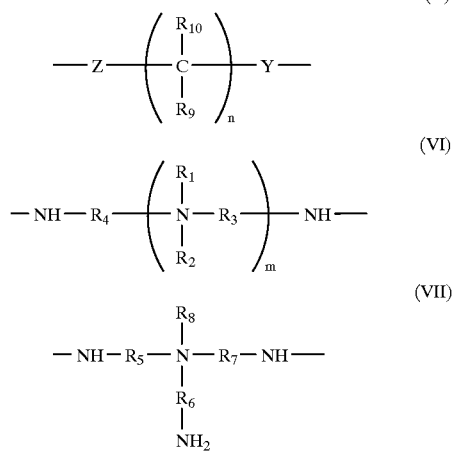

$$-Z-\left(\begin{array}{c} R_{10} \\ | \\ C \\ | \\ R_9 \end{array}\right)_n -Y- \quad (V)$$

$$-NH-R_4-\left(\begin{array}{c} R_1 \\ | \\ N-R_3 \\ | \\ R_2 \end{array}\right)_m -NH- \quad (VI)$$

$$-NH-R_5-\begin{array}{c} R_8 \\ | \\ N-R_7-NH- \\ | \\ R_6 \\ | \\ NH_2 \end{array} \quad (VII)$$

b) Z and Y are each, independently, selected from the group consisting of a valence bond, carbonyl and amine moieties;

c) each of the $R_1$, $R_2$, and $R_8$ functionalities is, independently, selected from the group consisting of hydrogen, and aliphatic hydrocarbons having less than about three carbon atoms;

d) each of the $R_3$, $R_4$, $R_5$, $R_6$, and $R_7$ functionalities is, independently, an aliphatic hydrocarbon having from one to five carbon atoms, or a valence bond;

e) each of the $R_9$ and $R_{10}$ functionalities, is, independently, selected from the group consisting of a hydrogen and hydroxy;

f) n is an integer equal to or greater than one; and g) m is an integer equal to or greater than two.

2. The product of claim 1 wherein the product is selected from polymers (i), the suitable comonomer is selected from the group consisting of a dicarboxylic acid, a dicarboxylic ester, a dicarboxylic chloride, a dicarboxylic anhydride, a dicarboxylic imidazolide, a dihalide, and a dialcohol, and the suitable comonomer has up to twenty carbon atoms.

3. The product of claim 2 wherein the suitable comonomer is selected from the group consisting of a dicarboxylic monosaccharide and a dicarboxylic ester monosaccharide.

4. The product of claim 3 wherein the suitable comonomer is glucaric acid or ethyl ester glucaric acid.

5. The product of claim 1 wherein the product is selected from polymers (i) and $R_3$ and $R_4$ are ethylene linkages.

6. The product of claim 5 wherein formula (VI) represents polyethylene hexamine.

7. The product of claim 1 wherein the product is selected from polymers (i) having a molecular weight of between 12,000 and 20,000 amu.

8. The product of claim 1 wherein the product is selected from polymers (ii).

9. The polymer of claim 8 wherein the carbonyl and amino units are selected from the group consisting of —CO—, —$NR_1R_2$—CO—O—$CR_1R_2$—, —$NR_1R_2$—$CR_1R_2$—, and —$NR_1R_2$—CO—$CR_1R_2$—CO—.

10. The polymer of claim 8 wherein formula (V) represents a compound selected from the group consisting of a dicarboxylic acid, a dicarboxylic ester, a dicarboxylic chloride, a dicarboxylic anhydride, a dicarboxylic imidazolide, a dihalide, and a dialcohol having up to twenty carbon atoms.

11. The polymer of claim 10 wherein formula (V) represents a compound selected from the group consisting of a dicarboxylic monosaccharide and a dicarboxylic ester monosaccharide.

12. The polymer of claim 11 wherein formula (V) represents glucaric acid or ethyl ester glucaric acid.

13. The polymer of claim 8 wherein $R_3$ and $R_4$ are ethylene linkages.

14. The polymer of claim 8 wherein formula (VI) represents polyethylene hexamine.

15. The polymer of claim 8 wherein the polymer has a molecular weight of between 12,000 and 20,000 amu.

16. The product of claim 1 wherein the product is poly(3', 6', 9', 12'-aza-tetradecylmethylene D-glucaramide).

* * * * *